(12) United States Patent
Xiao et al.

(10) Patent No.: US 6,504,076 B1
(45) Date of Patent: Jan. 7, 2003

(54) METHOD OF CONVERSION OF HEAVY AROMATICS

(75) Inventors: Xin Xiao, Houston, TX (US); James R. Butler, Webster, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 09/860,755

(22) Filed: May 18, 2001

(51) Int. Cl.⁷ .............................. C07C 5/52; C07C 4/18
(52) U.S. Cl. ......................................... 585/475; 585/489
(58) Field of Search ................................ 585/475, 484

(56) References Cited

U.S. PATENT DOCUMENTS 5,475,180 A    12/1995    Shamshoum et al. ....... 585/475

OTHER PUBLICATIONS

Unzelman, G.H., Reformulated Fuels–1: Reformulated Gasolines Will Challenge Product–Quality Maintenance, Oil & Gas Journal, Apr. 9, 1990, pp. 43–48.

*Primary Examiner*—Thuan D Dang
(74) *Attorney, Agent, or Firm*—Grady K. Bergen; Bradley A. Misley

(57) ABSTRACT

A method is provided for conversion of heavy alkylaromatic compounds, particularly those in the $C_8$–$C_{12}$ range, into more valuable aromatics of benzene, toluene and xylene utilizing a toluene disproportionation unit containing a nickel, palladium or platinum-modified mordenite catalyst. The method allows large amounts of these heavy alkylaromatic compounds to be processed without adversely affecting catalyst activity or catalyst life. This is accomplished by introducing the heavy alkylaromatic compounds into the reactor at constant reaction severity conditions and maintaining those conditions during conversion.

19 Claims, 1 Drawing Sheet

METHOD OF CONVERSION OF HEAVY AROMATICS

TECHNICAL FIELD

The invention relates generally to the conversion of heavy aromatic feedstreams, and more particularly to the conversion feedstreams containing $C_{8+}$ alkylaromatics through the use of mordenite catalysts.

BACKGROUND

The disproportionation of toluene involves a well known transalkylation reaction in which toluene is converted to benzene and xylene in accordance with the following reaction:

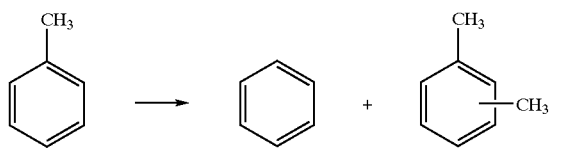

(1)

The reaction (1) is mildly exothermic.

Mordenite is one of a number of molecular sieve catalysts useful in the transalkylation of alkylaromatic compounds. Mordenite is a crystalline aluminosilicate zeolite exhibiting a network of silicon and aluminum atoms interlinked by oxygen atoms within the crystalline structure. For a general description of mordenite catalysts, reference is made to Kirk-Othmer, *Encyclopedia of Chemical Technology*, $3_{rd}$ edition, 1981, under the heading "Molecular Sieves," Vol. 15, pages 638–643, which is herein incorporated by reference. Mordenite, as found in nature or as synthesized to replicate the naturally occurring zeolite, typically exhibits a relatively low silica to alumina mole ratio of about 10 or less. Also known, however, are mordenite catalysts exhibiting a substantially lower alumina content. These aluminum deficient mordenite catalysts exhibit silica to alumina ratios greater than 10, ranging up to about 100, and may be prepared by direct synthesis as disclosed for example, in U.S. Pat. No. 3,436,174 to Sand or by acid extraction of a more conventionally prepared mordenite as disclosed in U.S. Pat. No. 3,480,539 to Voorhies. Both the typical and the aluminum deficient mordenites are known to be useful in the disproportionation of toluene.

General operating conditions relating to the disproportionation of toluene feedstock include temperatures ranging from about 200° C. to about 600° C. or above, and pressures ranging from atmospheric to perhaps 100 atmospheres or above. The specific catalyst, however, may impose constraints on reaction temperatures in terms of catalyst activity and aging characteristics. In general, the prior art suggests the use of relatively high temperatures when employing the high aluminum mordenites (low silica to alumina ratios) and somewhat lower temperatures when employing low alumina mordenites. Accordingly, where mordenite catalysts exhibiting high silica to alumina ratios have been employed in the transalkylation of alkylaromatics, it has been the practice to operate toward the lower end of the temperature range.

U.S. Pat. No. 4,665,258 to Butler, however, discloses a toluene disproportionation process employing an aluminum deficient mordenite catalyst, involving a temperature range of 370° C. to 500° C. The mordenite catalysts described therein exhibit silica/alumina ratios of at least 30 and, more desirably, within the range of 40–60. The toluene weight hourly space velocity (WHSV) may be greater than 1. Hydrogen is supplied to the reaction zone at a hydrogen/toluene mole ratio within the range of 3–6, at a pressure of 500 psi or more.

Butler '258 also discloses passing a hot preflush gas, nitrogen or hydrogen, to the reaction zone prior to initiating the disproportionation reaction. The preflush gas is heated to a temperature sufficient to substantially dehydrate the catalyst by the time the toluene feed is started. This measure enables the disproportionation process to initially be performed at a somewhat lower temperature and without reduction in toluene conversion. As the disproportionation proceeds, temperature progressively increases to maintain toluene conversion at the desired level, typically about 80 percent of theoretical U.S. Pat. No. 4,723,049 to Menard discloses toluene disproportionation carried out over aluminum deficient mordenite of the type disclosed in the aforementioned patent to Butler, with a reaction zone temperature of 370° C. to 500° C. Menard '049 employs an interruption procedure whereby the supply of toluene to the reaction zone is interrupted while the supply of hydrogen is continued. This mode of operation is disclosed to enhance the aging quality of the catalyst and show a reduction in reactor zone temperature without a corresponding decrease in toluene conversion.

It is also a common practice to promote an aluminum deficient mordenite catalyst with a catalytically active metallic content. For example, U.S. Pat. No. 3,476,821 to Brandenburg discloses disproportionation reactions employing mordenite catalysts having silica/alumina ratios within the range of 10–100 and preferably within the range of about 20–60. The mordenites are modified by the inclusion of a sulfided metal selected from the Group VIII metals. The especially preferred sulfided Group VIII metals are cobalt and nickel present in a concentration of 0.5–10 weight percent. Brandenburg '821 discloses temperature ranges from about 400° F.–750° F. The metal promoters are said to substantially increase activity and catalyst life, as indicated by runs extended over several hours or days.

As noted previously, hydrogen is commonly supplied along with toluene to the reaction zone. While the disproportionation reaction (1) does not involve chemical consumption of hydrogen, the use of hydrogen co-feed is generally considered to prolong the useful life of the catalyst, as disclosed, for example, in the above mentioned patent to Brandenburg '821. The amount of hydrogen supplied, which is normally measured in terms of the hydrogen/toluene mole ratio, is generally shown in the prior art to increase as temperature increases.

Bhavikatti, "Toluene Disproportionation Over Aluminum-Deficient and Metal-Loaded Mordenites. 1. Catalytic Activity and Aging", Ind. Eng. Chem. Prod. Res. Dev. 1981, 20, 102–105, discloses toluene disproportionation at 400° C. over mordenite catalysts having silica/alumina mole ratios ranging from 12 to 61 at atmospheric pressure and a space velocity (WHSV) of 1. Bhavikatti indicates that an increase in the silica/alumina mole ratio decreases catalyst activity, while aging quality is increased (i.e. lowering aging rates). Catalyst decay was also suppressed by loading mordenites with nickel.

U.S. Pat. No. 3,562,345 to Mitsche discloses the use of molecular sieves such as mordenite catalysts in the disproportionation of toluene. The catalysts are characterized by a silica/alumina mole ratio of from about 6 to about 12, pore openings of from about 3 to about 18 angstroms and the incorporation of catalytically active metallic materials in the oxidized or reduced state, particularly Group VIB and Group VIII metals including molybdenum, tungsten, chromium, iron, nickel, cobalt, platinum, palladium, ruthenium, rhodium, osmium, and iridium. Mitsche '345 discloses transalkylation at temperatures from about 200° C. to about 480° C. and gives specific examples of transalkylation of toluene at temperatures of 420° C. to 450° C.

U.S. Pat. No. 3,677,973 to Mitsche, discloses the use of mordenite catalysts composited with an alumina salt providing a silica/alumina mole ratio of about 10 to about 30 in the disproportionation of toluene. The reaction conditions proposed in Mitsche '973 appear similar to those set forth in the aforementioned Mitsche '845 patent and, like the former patent, Mitsche '973 discloses incorporating Group VIB and Group VIII metals into the catalyst.

U.S. Pat. No. 4,151,120 to Marcilly discloses a process for the manufacture of a hydrocarbon conversion catalyst involving incorporating cobalt, nickel, silver or palladium in a mordenite catalyst having a silica/alumina mole ratio within the range of 10–100. Following incorporation of the metal into the mordenite, the catalyst is dried and subjected to a dry calcination procedure at a temperature within the range of 300° C.–700° C. in the presence of an inert or oxidizing gas having a moisture content of less than 1 percent. Marcilly '120 discloses various examples of the dismutation of toluene under reaction conditions 420° C., 30 bars, a space velocity (WHSV) of 5 and a hydrogen/hydrocarbon mole ratio of 5.

U.S. Pat. No. 4,723,048 to Dufresne discloses a process for the dismutation of toluene employing a zeolite catalyst modified by the inclusion of metals. The catalyst is described as a sodium-containing mordenite in the nature of a so-called "wide pore" mordenite, i.e., mordenite with main pores exhibiting a diameter of 7–10 Angstroms or "small pore" mordenite, mordenites with main pores exhibiting a diameter of 4–6 Angstroms. The mordenites are treated to extract sodium therefrom to provide not more than one percent by weight sodium ions and preferably not more than 0.5 percent by weight sodium ions.

Of the aforementioned references, none of them teach or suggest the disproportionation or conversion of toluene feedstock containing other heavy aromatic compounds, such as trimethylbenzenes and ethyltoluenes. In the reforming process, heavier aromatic compounds, i.e. aromatic compounds of $C_8$ or greater, are often produced that have lesser value than other lighter aromatic compounds, such as benzene and xylene. Typically, these heavier aromatic reformates are used in gasoline blending along with toluene. Reducing the amounts of these heavier aromatics in the gasoline pool is beneficial, however, as more premium gasoline can be produced. Additionally, it is a great advantage if these heavier aromatics can be converted into more commercially valuable products, such as benzene, toluene and xylene.

U.S. Pat. No. 5,475,180 to Shamshoum, discloses the conversion of heavier aromatics during the disproportionation of toluene using a nickel-promoted mordenite catalyst. Specifically, this reference discloses introducing a heavy aromatic feed along with pure toluene during toluene disproportionation while maintaining toluene conversion levels and without adversely affecting catalyst activity and aging quality. While Shamshoum '180 discloses the conversion of heavy aromatic compounds, the amount of heavy aromatics that can be processed is limited. Because Shamshoum '180 is concerned with the constant conversion of toluene, toluene must make up the majority of the feed. Shamshoum '180 does not disclose processing feed streams composed of large amounts of heavy aromatics, or feedstreams that are made up primarily or entirely of such heavy aromatics. It would therefore be beneficial to provide a method of converting heavy aromatic compounds in large quantities and without adversely affecting catalyst activity or reducing catalyst life for use in toluene disproportionation.

SUMMARY

A method of converting a feed of heavy aromatics composed primarily of $C_{8+}$ alkylaromatic compounds to produce products of benzene, toluene and xylene is provided. This is accomplished by providing a reaction zone containing a mordenite catalyst. The feed is introduced into the reaction zone so that the feed contacts the mordenite catalyst under selected conditions that are based upon reaction zone conditions necessary to obtain a desired conversion during disproportionation of substantially pure toluene using the mordenite catalyst.

The conversion of the feed within the reaction zone is allowed to occur to provide an established conversion of the feed while the reaction zone is initially at the selected conditions. The reactor conditions are adjusted as necessary to generally maintain the conversion of the feed at the established conversion. Conversion products are removed from the reaction zone. In specific embodiments, the mordenite catalyst may be a nickel, palladium or platinum-containing mordenite catalyst.

In another embodiment, a method of converting a feed of heavy aromatics composed primarily of $C_{8+}$ alkylaromatic compounds in a toluene disproportionation reaction unit for disproportionating substantially pure toluene to produce benzene, toluene and xylene from the feed in a continuous process without substantially reducing catalyst activity for use in toluene disproportionation is provided. This is accomplished by providing a reaction zone of the reaction unit containing a catalyst selected from a group consisting of a nickel-containing mordenite catalyst, a platinum-containing modenite catalyst and palladium-containing mordenite catalyst for disproportionating substantially pure toluene.

The feed is introduced into the reaction zone so that the feed contacts the catalyst under selected conditions that are based upon reaction zone conditions necessary to obtain a desired conversion during disproportionation of substantially pure toluene using the catalyst. The conversion of the feed within the reaction zone is allowed to occur to provide an established conversion of the feed while the reaction zone is initially at the selected conditions. Reactor conditions are adjusted as necessary to generally maintain the conversion of the feed at the established conversion. Conversion products are removed from the reaction zone.

Toluene feed can be introduced into the reaction zone along with the heavy aromatic feed. In such cases, the heavy aromatics can make up at least 15%, 25%, 35%, 50% or 75% by total weight of the feed introduced into the reaction zone. The heavy aromatics can also make up substantially the entire feed introduced into the reaction zone.

In yet another embodiment, a method of converting a feed of heavy aromatics composed primarily of $C_{8+}$ alkylaromatic compounds in a toluene disproportionation reaction unit for proportionating substantially pure toluene to produce benzene, toluene and xylene from the feed in a continuous process in which the heavy aromatics make up at least 35% by total weight of the feed, with the balance of the feed being toluene, and without substantially reducing catalyst activity for use in disproportionating substantially pure toluene is provided. This is accomplished by providing a reaction zone of the reaction unit containing a catalyst selected from a group consisting of a nickel-containing mordenite catalyst, a platinum-containing modenite catalyst and palladium-containing mordenite catalyst for disproportionating substantially pure toluene.

The feed is introduced into the reaction zone so that the feed contacts the catalyst under selected conditions that are based upon reaction zone conditions necessary to obtain a desired conversion during disproportionation of substantially pure toluene using the catalyst. The conversion of the feed within the reaction zone is allowed to occur to provide an established conversion of the feed while the reaction zone is initially at the selected conditions. Reactor conditions are adjusted as necessary to generally maintain the conversion of the feed at the established conversion, and conversion products are removed from the reaction zone.

In specific embodiments, where a nickel-containing mordenite catalyst is utilized, the catalyst may contain from about about 0.5% to about 1.5% by weight nickel. Where a palladium-containing catalyst is used, it may contain from about 0.1% to about 0.5% by weight palladium. And where a platinum-containing mordenite catalyst is used, it may contain from about 0.1% to about 0.5% by weight platinum. The catalyst may have a silica to alumina molar ratio of from about 10:1 to about 60:1.

The reaction zone may be opened at a temperature of from about 250 to about 500° C., and a pressure of at least about 150 psig. Adjustment of reactor conditions to maintain the conversion of the feed at the established conversion can be achieved by adjusting the temperature of the reaction zone.

The invention also encompasses the conversion products produced from the above methods.

BRIEF DESCRIPTION OF THE DRAWINGS

For a more complete understanding of the present invention, and the advantages thereof, reference is now made to the following descriptions taken in conjunction with the accompanying figures, in which.

DETAILED DESCRIPTION

Figure 1:
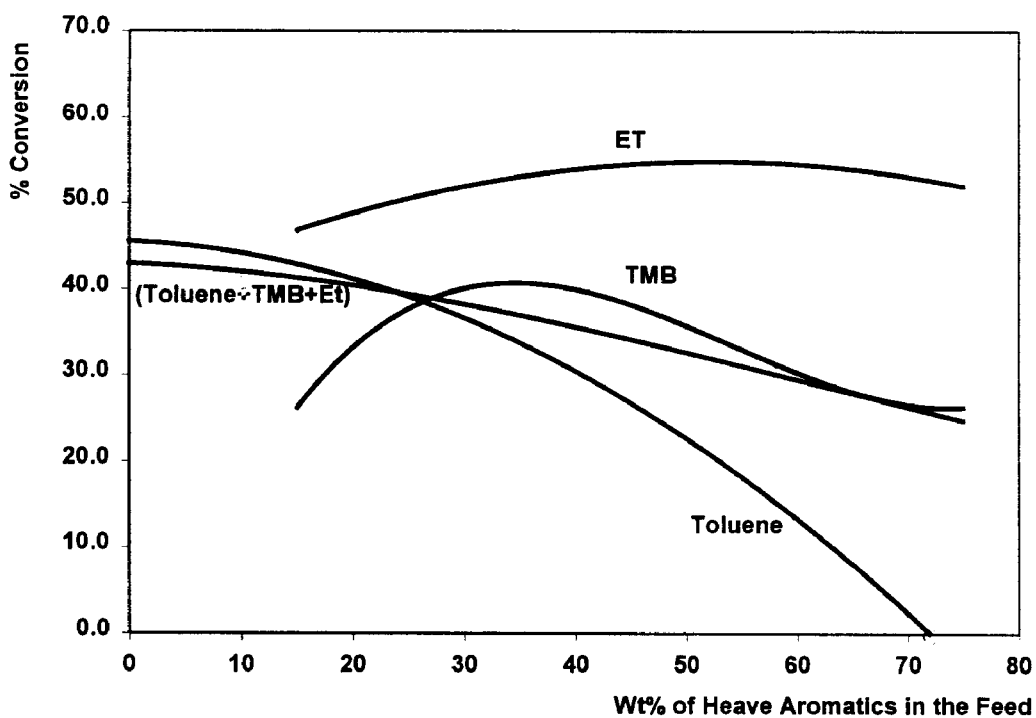
FIG. 1 is a plot of the conversion of toluene, ethyltoluene and trimethylbenzene as a function of mixed feeds of heavy aromatics and toluene at different feed ratios utilizing a nickel-modified mordenite catalyst.

It has been found that heavy aromatic compounds can be processed to form more desirable compounds through the use of mordenite catalysts useful in the disproportionation of toluene. In particular, the present invention has application to those heavy aromatic compounds that are composed primarily of $C_{8+}$ alkylaromatics. These may be the heavy aromatic reformate cut obtained from a naptha reformer or the heavier byproducts obtained from toluene disproportionation. It may be desirable to specifically limit the heavy alkylaromatics to those in the $C_8$ to $C_{12}$ range. This can be achieved by boiling point fractionation, which is well known to those skilled in the art. Such compounds may include ethylbenzene, ortho-rich mixed xylenes, trimethylbenzene, ethyl toluene, n-propyl benzene, cumene, diethylebenzene, tetramethylbenzene and dimethylethylbenzene, as well as other alkylaromatics in the $C_{10}$ to $C_{12}$ range.

Such compounds can be processed through the same reaction zone used in the disproportionation of toluene to produce benzene, toluene and xylene. The heavy aromatics can either be introduced into the reaction zone with a toluene feedstock or can be introduced into the reaction zone alone. The present invention has particular application in processing heavy aromatics that make up at least 15% by weight of the total feed introduced into the reaction zone, with heavy aromatics making up at least about 25%, 35%, 50%, 75% and even 100% by weight of total feed being readily processable. In many instances, it may be desirable to process the heavy aromatics in larger quantities of at least about 40% by weight of the total feed. This can be accomplished without adversely affecting the catalyst activity or reducing the life of the catalyst for use in the disproportionation of toluene.

In the present invention, a reaction zone containing a metal-promoted mordenite catalyst is utilized. The reaction zone is operated under disproportionation conditions including a temperature range of 250° C. to 500° C. and a pressure of from about 150 psig to about 800 psig. The liquid hourly space velocity will typically be in the range of from about 0.1/hr to about 10/hr, with from about 1/hr to about 5/hr being preferred. Contemporaneously, hydrogen is cored to the reaction zone to provide a hydrogen environment. Hydrogen is typically fed to the reactor in amounts of about 0.2 to about 2.5 std $m^3$/kg liquid feed.

The mordenite catalyst employed in the present invention is modified by the inclusion of a metallic hydrogenation component. Specifically these include the Group VIIIB metals of nickel, palladium and platinum. Such modification of the mordenite catalysts enhances catalyst activity and aging, and yields toluene conversion rates in toluene disproportionation of about 30% to about 55%, with preferably from about 42% to about 48% conversion at relatively low temperature and with a low rate of catalytic deactivation. The mordenite catalysts employed in the present invention preferably exhibit, but are not limited to, a silica to alumina mole ratio of from about 10:1 to about 60:1, with from 16:1 to about 29:1 being a preferred range. With respect to metal content, those mordenite catalysts containing nickel preferably contain nickel in the amount of from 0.5% to about 1.5% by weight, with nickel in the amount of about 1.0% by weight being particularly well suited. Those mordenite catalysts containing palladium preferably contain from about 0.1 to about 0.5% by weight palladium, and those containing platinum preferably contain from about 0.1% to about 0.5% by weight platinum. It should be pointed out that when using palladium or platinum-containing mordenite catalysts, pressures within the reaction zone are usually reduced to reduce aromatic ring saturation. Reactor pressures for mordenite catalysts containing nickel are usually maintained at from about 400 to 800 psig, while reactor pressures for mordenite catalysts containing palladium or platinum are usually maintained at from about 150 to about 600 psig.

The present invention has particular application in recycling heavy aromatics to a toluene disproportionation unit in a continuous process to thereby increase the number and amount of desirable aromatic products produced in naptha reformation or toluene disproportionation processes. In the preferred embodiment, conversion of the heavy aromatics is carried out by initially introducing a substantially pure toluene feedstock to a reaction zone of a toluene disproportionation unit containing a metal-modified mordenite catalyst at the desired reaction conditions, as discussed above. Reaction conditions, particularly temperature, are adjusted as necessary to achieve the desired conversion of the substantially pure toluene. A typical target conversion of toluene may be from about 30 to 55%, more specifically from 42 to 48%.

Once the desired level of conversion for the substantially pure toluene has been achieved, the heavy aromatic component to be converted, which is preferably composed of the $C_8$ to $C_{12}$ alkylaromatics, is feed into the reaction zone of the toluene disproportionation unit. The heavy aromatic stream may contain up to 20% by weight $C_6$ to $C_8$ aromatics. This is done while maintaining the conditions selected for the disproportionation of the pure toluene to achieve the desired toluene disproportionation target level. The introduction of the heavy aromatics into the reaction zone may be accomplished by combining the heavy aromatics with the pure toluene feedstock in desired proportions or by independently introducing the heavy aromatics into the reaction zone.

Once the heavy aromatics are introduced into the reaction zone and come into contact with the mordenite catalyst under the selected conditions, the conversion of the heavy aromatics is allowed to proceed and the conversion products are removed from the reaction zone. The conversion of the heavy aromatics consists of transalkylation/dealkylation reactions that result in the formation of primarily benzene, xylene and toluene. In conversion of heavy aromatics where toluene is also used as a co-feed, the net conversion of toluene may decrease, as toluene is one of the products produced from the conversion of the heavy aromatic stream. Thus, the reduction in toluene conversion is not due to catalyst deactivation but can be explained by the following reactions:

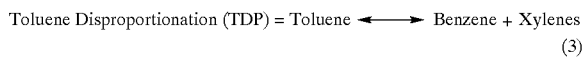
Toluene Disproportionation (TDP) = Toluene ⇌ Benzene + Xylenes (2)

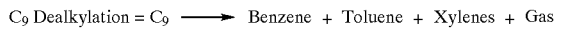
$C_9$ Dealkylation = $C_9$ → Benzene + Toluene + Xylenes + Gas (3)

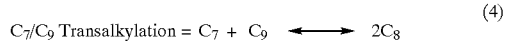
$C_7/C_9$ Transalkylation = $C_7$ + $C_9$ ⇌ $2C_8$ (4)

As can be seen in Equation 2, toluene disproportionation is a reversible reaction driven by equilibrium. When $C_{8+}$ aromatics exist in the stream, they undergo transalkylation/dealkylation reactions that lead to benzene, toluene and xylenes, as seen in Equations 3 and 4. In mixed streams, the produced benzene and xylenes push the toluene disproportionation reaction to the left. Moreover, toluene is produced from the $C_9$ stream. The net toluene conversion should therefore decrease due to these effects after the heavy aromatic feed is introduced.

As the heavy aromatics are initially converted and withdrawn, the conversion of the feed is monitored while the reactor is maintained at the selected conditions for the disproportionation of pure toluene. This provides an established conversion rate for the new feed containing the heavy aromatics. The conversion of individual components depends on the feed composition due to equilibrium. Constant reaction severity is maintained by process conditions so that conversion of each individual component remains constant after the reaction reaches steady state upon change in feed composition. To maintain these constant conversions, one or more of the process variables, e.g., temperature, is adjusted to compensate for the slow catalyst deactivation. The reaction severity can be easily checked using a pure feed, i.e. toluene. In this case, the conversion would be on target if the feed were switched to pure toluene. Once this new conversion rate is determined, the reactor conditions are adjusted accordingly to maintain a generally constant conversion or reaction severity so that the established conversion of the reactor feed including the heavy aromatics is maintained. In most instances, the conversion of the heavy aromatics can be maintained by incrementally increasing the temperature of the reactor.

It has been found that by maintaining constant reaction severity while converting the heavy aromatics, the rate of catalyst deactivation can be maintained as it would during the disproportionation of pure toluene. Thus, the life of the catalyst is not decreased by any greater degree than it would during normal toluene disproportionation operations. This has been confirmed in tests where the disproportionation of pure toluene has been interrupted by the introduction of a heavy aromatic feed in a mordenite-containing disproportionation reactor where the conversion heavy aromatic feed is carried out at a constant reaction severity, and then the reactor is switched back to the disproportionation of pure toluene. In such tests, when the reactor is switched back to the disproportionation of the pure toluene, the conversion rate of the toluene has generally matched that of the initial toluene disproportionation prior to the interruption by the heavy aromatic feed.

In this way, large amounts of heavy aromatics, including up to 100% heavy aromatics, can be converted through the use of a toluene disproportionation unit without adversely affecting catalyst activity or catalyst life. The disproportionation unit can be easily switched back and forth between the disproportionation of pure toluene and the conversion of heavy aromatic components, used either as a co-feed or as a feed composed entirely of the heavy aromatics. The ability to convert large quantities of such heavy aromatics without significant disruption of toluene disproportionation operations is a great advantage. Additionally, the process allows the conversion of lesser valued heavy aromatics into the higher valued aromatic products of benzene, toluene and xylene. The conversion allows the conversion of these heavy aromatics, with or without toluene co-feed. The following examples better serve to illustrate the invention.

EXAMPLE 1

A 100% heavy aromatic feed was introduced into a toluene disproportionation reactor containing a mordenite catalyst. During startup, the reactor was initially packed and purged with nitrogen. Hydrogen was then introduced at a flow of 1 L/min and pressure was increased to 600 psig. The temperature was ramped up at 50° C./h to 200° C. (390° F.) and held overnight. The temperature was then ramped at the same rate to 250° C. (485° F.) and held for two hours. A pure toluene feed was started at 1.5 mL/min and hydrogen was feed into the reactor at a hydrocarbon ratio of 1:1 for the startup phase. Temperature was then adjusted to achieve 47% (53% effluent) conversion of toluene. When the non-aromatics selectivity dropped below 1%, the $H_2$/HC mole ratio was increased to 2:1. Temperature was then adjusted to reach a 45–47% conversion of toluene.

The mordenite catalyst was a nickel-promoted mordenite catalyst having a nickel content of about 1.0% by weight under temperature and pressure conditions of 753–817 ° F. (400–436° C.) and 500–800 psig. Hydrogen was fed to the reactor at a rate of about 2500 SCF/BBL of feed and the feedstock liquid hourly space velocity (LHSV) was about 2/hr. At the $70^{th}$ day of operation, the feed was switched from a substantially pure toluene feed to a heavy aromatic feed. The heavy aromatic feed stream had about 76.1% $C_9$ alkylbenzenes, about 6.7% $C_{10}$ aromatics, about 5.6% $C_{11+}$ aromatics, and about 11.0% xylenes and about 1.0% toluene by weight. Table 1 lists the detailed compositions of the heavy aromatic feed and a typical product.

TABLE 1

| Composition | Molecular Weight | Feed Wt % | Product, Wt % |
|---|---|---|---|
| Nonaromatics | 79 | 0.0246 | 5.5219 |
| Benzene | 78 | 0.0056 | 2.1909 |
| Toluene | 92 | 1.0086 | 12.2213 |
| Ethylbenzene | 106 | 0.0986 | 2.2595 |
| p-xylene | 106 | 0.5243 | 5.1189 |
| m-xylene | 106 | 1.4795 | 11.4923 |
| o-xylene | 106 | 9.0606 | 5.1201 |
| Cumene | 120 | 0.5616 | 0.0027 |
| n-propylbenzene | 120 | 5.9406 | 0.0603 |
| Ethyltoluenes | 120 | 31.7556 | 11.7561 |
| 1,3,5-TMB* | 120 | 9.4735 | 7.7936 |
| 1,2,4-TMB* | 120 | 27.4495 | 19.1458 |
| 1,2,3-TMB* | 120 | 0.9528 | 1.6098 |
| DEBs** | 132 | 1.1045 | 0.5521 |
| Bu-BZs† | 134 | 0.0000 | 0.0000 |
| Other $C_{10}$ | 134 | 5.5721 | 3.8233 |
| Heavies $C_{11+}$ | ≧148 | 4.9879 | 11.3315 |

*TMB = trimethylbenzene
**DEB = diethylbenzene
†Bu-BZs = butylbenzenes

About two-thirds of ethyltoluenes, a quarter of TMBs and one half of DEBs were converted. Products were toluene, xylene, a small amount of benzen, EB and nonaromatics. Almost all n-propylbenzene and cumene were converted. Toluene, xylenes and trimethylbenzenes have chains too short to have a comparable dealkylation rate. It was also observed that higher pressure increased conversions, while lower pressure decreased conversions.

The reactor effluent composition was also recalculated on a volume % basis, comparing toluene and the heavy aromatic feeds. The results are presented in Table 2 and show that the heavy aromatic conversion had a 6.1% volume expansion plus 45.8 SCF/bbl fuel gas on a single pass reaction. Gas and nonaromatic yields were also higher than that of the TDP, as expected from dealkylation.

TABLE 2

| FEED TYPE | | TOLUENE | HEAVY AROMATICS |
|---|---|---|---|
| Feed | | | |
| Toluene | Vol. % | 100 | 0 |
| Heavy Aromatics | Vol. % | 0 | 100 |
| Product Based on Feed | | | |
| Dry Gas, std ft³/bbl | ft³/bbl | 7.2 | 45.8 |
| LPG ($C_3$—$C_5$) | Vol % | 2.1 | 10.1 |
| Non-Aromatics (~Hexanes) | Vol % | 0.3 | 1.6 |
| Benzene | Vol % | 19.1 | 2.2 |
| Toluene | Vol % | 52.3 | 12.2 |
| EB | Vol % | 0.5 | 2.3 |
| Mixed Xylenes | Vol % | 22.3 | 21.6 |
| $C_9$'s | Vol % | 5.3 | 40.7 |
| $C_{10+}$ | Vol % | | 15.4 |
| Summary of Liquid Products | Vol % | 101.9 | 106.1 |

EXAMPLE 2

Heavy aromatic feed was introduced into a toluene disproportionation unit containing a mordenite catalyst along with toluene with the heavy aromatic component varying in the amounts of 0%, 15%, 25%, 35%, 50% and 75% by weight of the mixture. The composition of the heavy aromatic feed was the same as that listed in Table 1 of Example 1. A nickel-modified mordenite catalyst containing about 0.93% by weight nickel was used as the catalyst. Startup procedures were similar to those described for Example 1.

After about two weeks of disproportionation of the pure toluene feed (i.e. heavy aromatics=0%), a mixture of 25% by weight heavy aromatics and 75% by weight toluene was fed to the reactor keeping the reaction conditions the same as that for the pure toluene. Due to equilibrium limitations, conversions of toluene and other components were different after the feed changes. This new conversion was monitored to provide a new established conversion rate for the new feed composition. Reaction temperature was then adjusted to maintain constant conversion based on this established conversion. Similar procedures were followed for subsequent changes in feed composition, with reaction conditions kept the same initially as the prior feed to determine a new established conversion rate.

FIG. 1 shows the conversion of toluene, ethyltoluene and trimethylbenzene as a function of heavy aromatic feed. Toluene conversion dropped from 46.3% to 38.7% when 25 wt % heavy aromatics was introduced while maintaining the reaction conditions. $C_8$ was the main product in the stream. With up to 50% by weight heavy aromatics in the feed, only minor changes were observed to the yield of mixed xylenes. This was a result of lower conversion of toluene and higher conversion of $C_9$ aromatics. Benzene yield decreased dramatically when heavy aromatic feed increased. Ethylbenzene, nonaromatics and $C_{10+}$ heavies changed slightly.

The toluene conversion continued to drop with higher amounts of heavy aromatics in the feed. At 75% heavy aromatics, the amount of toluene consumed was the same as the toluene produced. Conversions of ET and TMB were 52.5% and 26.2%, respectively. Feed was converted mostly to xylenes and benzene as net products. Each step of feed change was continued for two weeks to obtain the catalyst deactivation rate. To confirm the concept of "constant severity," feed was changed back to toluene after twelve weeks. The toluene conversion was found to be 46.8%. No difference on catalyst deactivation rate was observed among the TDP mode and different levels of heavy aromatics in the feed.

EXAMPLE 3

Heavy aromatic feed at different feed ratios with toluene were fed into a toluene disproportionation unit containing a mordenite catalyst. The heavy aromatic component was varied in amounts of 0%, 15% and 25% by weight of the mixture. The heavy aromatic feed had the composition shown in Table 3 below.

TABLE 3

| | Heavy Aromatic Feed (wt. %) |
|---|---|
| Nonaromatics | 0.0188 |
| Benzene | 0.0012 |
| Toluene | 1.0000 |
| Ethylbenzene | 0.0442 |
| p-xylene | 0.4287 |
| m-xylene | 0.3426 |
| o-xylene | 6.9010 |
| Cumene | 0.6583 |
| n-propylbenzene | 6.2929 |

TABLE 3-continued

| | Heavy Aromatic Feed (wt. %) |
|---|---|
| Ethyltoluenes | 27.2315 |
| 1,3,5-TMB* | 8.0594 |
| 1,2,4-TMB* | 26.9521 |
| 1,2,3-TMB* | 5.9870 |
| DEBs** | 1.6482 |
| Bu-BZs† | 0 |
| Other $C_{10}$ | 6.9403 |
| Heavies $C_{11+}$ | 7.4938 |

*TMB = trimethylbenzene
**DEB = diethylbenzene
†Bu-BZs = butylbenzenes

The catalyst used was a nickel-modified mordenite catalyst containing 0.93% by weight nickel. Startup procedures were similar to those of Example 1.

After about three weeks of pure toluene feed (0% heavy aromatics), the feed was switched to a mixture of 15% by weight heavy aromatics and 85% by weight toluene keeping the reaction conditions the same as that for the pure toluene. Due to equilibrium limitations, conversions of toluene and other components were different after the feed was changed. This new conversion was monitored to provide a new established conversion rate for the new feed composition. Reaction temperature was then adjusted to maintain constant conversion based on this established conversion rate. Similar procedures were followed for subsequent the changes in feed composition to 25% by weight heavy aromatics and 75% by weight toluene.

Table 4 lists conversions for TMB, ET and toluene as a function of weight percent of heavy aromatics in the feed. Feed was converted mostly to xylenes and benzene as net products. The data were the average of at least ten data points.

TABLE 4

| Wt. % Heavy Aromatics in Feed | 0% | 15% | 25% |
|---|---|---|---|
| Conversion, wt % | | | |
| TMB | | 22.52 | 35.82 |
| ET | | 32.87 | 50.93 |
| Toluene | 46.8 | 40.59 | 37.32 |
| Toluene + TMB + Et | | 39.11 | 38.04 |
| Deactivation Rate, ° F./day | 3.6 | 3.8 | 1.0 |

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of converting a feed of heavy aromatics composed primarily of $C_{8+}$ alkylaromatic compounds to produce products of benzene, toluene and xylene, in which the heavy aromatics make up at least 15% by total weight of the feed, the balance of the feed composed primarily of toluene, the method comprising:

providing a reaction zone containing a mordenite catalyst;
   introducing the feed into the reaction zone so that the feed contacts the mordenite catalyst under initial reaction zone conditions necessary to obtain a target toluene conversion between 30% and 55% during disproportionation of substantially pure toluene using the mordenite catalyst;

allowing conversion of the feed within the reaction zone to occur to provide an established conversion of the feed, including an established toluene conversion, while the reaction zone is at the initial reaction zone conditions;

adjusting reactor conditions to generally maintain the conversion of the feed at the established conversion; and removing conversion products from the reaction zone;
   wherein the established toluene conversion is at least 13% less than the target toluene conversion; and
   wherein the toluene conversion decreases with an increased percentage of feed composed of heavy aromatics.

2. The method of claim 1, wherein the heavy aromatics make up at least 25% by total weight of the feed introduced into the reaction zone.

3. The method of claim 1, wherein the heavy aromatics make up at least 35% by total weight of the feed introduced into the reaction zone.

4. The method of claim 1, wherein the heavy aromatics make up at least 50% by total weight of the feed introduced into the reaction zone.

5. The method of claim 1, wherein the heavy aromatics make up at least 75% by total weight of the feed introduced into the reaction zone.

6. The method of claim 1, wherein the heavy aromatics make up substantially the entire feed introduced into the reaction zone.

7. The method of claim 1, wherein the mordenite catalyst is a nickel, palladium or platinum-containing mordenite catalyst.

8. The method of claim 1, wherein the mordenite catalyst has a silica to alumina molar ratio of from about 10:1 to about 60:1.

9. The method of claim 1, wherein the mordenite catalyst is a nickel-containing mordenite catalyst containing from about 0.5% to about 1.5% by weight nickel.

10. The method of claim 1, wherein the mordenite catalyst is a palladium-containing mordenite catalyst containing from about 0.1% to about 0.5% by weight palladium.

11. The method of claim 1, wherein the mordenite catalyst is a platinum-containing mordenite catalyst containing from about 0.1% to about 0.5% by weight platinum.

12. The method of claim 1, wherein the reaction zone is operated at a temperature of from about 250 to about 500° C., and a pressure of at least about 150 psig.

13. The method of claim 1, wherein adjusting reactor conditions is achieved by adjusting the temperature of the reaction zone.

14. A method of converting a feed of heavy aromatics composed primarily of $C_{8+}$ alkylaromatic compounds in a toluene disproportionation reaction unit for disproportionating substantially pure toluene to produce benzene, toluene and xylene from the feed in a continuous process in which the heavy aromatics make up at least 25% by total weight of the feed, the balance of the feed composed primarily of toluene, without substantially reducing catalyst activity for use in toluene disproportionation, the method comprising:

providing a reaction zone of the reaction unit containing a catalyst selected from a group consisting of a nickel-containing mordenite catalyst, a platinum-containing modenite catalyst and palladium-containing mordenite catalyst for disproportionating substantially pure toluene;

introducing the feed into the reaction zone so that the feed contacts the catalyst under initial conditions that are based upon reaction zone conditions necessary to obtain a target conversion between 30% and 55% during disproportionation of substantially pure toluene using the catalyst;

allowing conversion of the feed within the reaction zone to occur to provide an established conversion of the feed, including an established toluene conversion, while the reaction zone is initially at the initial reaction zone conditions;

adjusting reactor conditions to generally maintain the conversion of the feed at the established conversion; and removing conversion products from the reaction zone;

wherein the established toluene conversion is at least 16% less than the target toluene conversion; and wherein the toluene conversion decreases with an increased percentage of feed composed of heavy aromatics.

15. The method of claim 14, wherein the heavy aromatics make up at least 50% by total weight of the feed introduced into the reaction zone.

16. The method of claim 14, wherein the heavy aromatics make up at least 75% by total weight of the feed introduced into the reaction zone.

17. The method of claim 14, wherein the reaction zone is operated at a temperature of from about 250 to about 500° C., and a pressure of at least about 150 psig.

18. The method of claim 14, wherein adjusting reactor conditions is achieved by adjusting the temperature of the reaction zone.

19. A method of converting a feed of heavy aromatics composed primarily of $C_{8+}$ alkylaromatic compounds in a toluene disproportionation reaction unit for disproportionating substantially pure toluene to produce benzene, toluene and xylene from the feed in a continuous process in which the heavy aromatics make up at least 35% by total weight of the feed, with the balance of the feed being toluene, and without substantially reducing catalyst activity for use in disproportionating substantially pure toluene, the method comprising:

providing a reaction zone of the reaction unit containing a catalyst selected from a group consisting of a nickel-containing mordenite catalyst, a platinum-containing modenite catalyst and palladium-containing mordenite catalyst for disproportionating substantially pure toluene;

introducing the feed into the reaction zone so that the feed contacts the catalyst under initial conditions that are based upon reaction zone conditions necessary to obtain a target conversion between 30% and 55% during disproportionation of substantially pure toluene using the catalyst;

allowing conversion of the feed within the reaction zone to occur to provide an established conversion of the feed while the reaction zone is at the initial conditions;

adjusting reactor conditions to generally maintain the conversion of the feed at the established conversion; and removing conversion products from the reaction zone;

wherein the established toluene conversion is less than the target toluene conversion; and wherein the toluene conversion decreases with an increased percentage of feed composed of heavy aromatics.

\* \* \* \* \*